US009654949B2

(12) United States Patent
Phan et al.

(10) Patent No.: US 9,654,949 B2
(45) Date of Patent: May 16, 2017

(54) AUTOMATIC CONSTRUCTION OF PERSONALIZED, PEER-DERIVED MESSAGES FOR MOBILE HEALTH APPLICATIONS

(71) Applicant: Samsung Electronics Co., Ltd., Suwon-si (KR)

(72) Inventors: Thomas Phan, Mountain View, CA (US); Juhan Lee, Mountain View, CA (US)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 14/985,222

(22) Filed: Dec. 30, 2015

(65) Prior Publication Data

US 2017/0094487 A1 Mar. 30, 2017

Related U.S. Application Data

(60) Provisional application No. 62/233,237, filed on Sep. 25, 2015.

(51) Int. Cl.
*H04W 4/00* (2009.01)
*H04W 4/18* (2009.01)
(Continued)

(52) U.S. Cl.
CPC .......... *H04W 4/18* (2013.01); *G06F 17/3053* (2013.01); *G06F 17/30528* (2013.01);
(Continued)

(58) Field of Classification Search
USPC ........................................................ 455/466
See application file for complete search history.

(56) References Cited

U.S. PATENT DOCUMENTS 8,918,473 B1    12/2014  O'Connor
2011/0087076 A1  4/2011  Brynelsen et al.
(Continued)

FOREIGN PATENT DOCUMENTS

WO    WO2006/094288 A2    9/2006
WO       2008152136 A1   12/2008
WO       2014051870 A1    4/2014

OTHER PUBLICATIONS

"The Potential Impact of Intelligent Systems for Mobile Health Self-Management Support: Monte Carlo Simulations of Text Message Support for Medication Adherence," Annals of Behavioral Medicine: J. Piette, K. Farris, S. Newman, L. An, J. Sussman, and S. Singh; vol. 49, issue 1, Feb. 2015; 11 Pages.

(Continued)

*Primary Examiner* — Joel Ajayi

(57) ABSTRACT

A method is implemented by at least one server. The method includes obtaining a set of users as a function of profile records regarding a plurality of users. The method includes defining a subset of the users as a peer group based on peer group formation features by applying a clustering algorithm to profile records of the set of users. The method includes calculating a peer group metric value for the peer group based on behaviors of the subset of users in the peer group. The method includes calculating a user metric value for a target-user included in the subset based on behavior of the target-user. The method includes constructing a message relating the patient metric value to the peer group metric value.

21 Claims, 8 Drawing Sheets

(51) Int. Cl.
*H04W 4/20* (2009.01)
*G06F 19/00* (2011.01)
*G06F 17/30* (2006.01)
*H04L 29/08* (2006.01)

(52) U.S. Cl.
CPC ........ *G06F 19/3418* (2013.01); *H04L 67/306* (2013.01); *H04W 4/206* (2013.01)

(56) References Cited

U.S. PATENT DOCUMENTS

| | | |
|---|---|---|
| 2011/0093295 A1 | 4/2011 | Mankad et al. |
| 2012/0330678 A1 | 12/2012 | Kobylevsky et al. |
| 2013/0091545 A1 | 4/2013 | Macdonald et al. |
| 2014/0074896 A1 | 3/2014 | Bushman et al. |

OTHER PUBLICATIONS

Notification of Transmittal of the International Search Report and the Written Opinion of the International Searching Authority, or the Declaration dated Dec. 5, 2016 in connection with International Application No. PCT/KR2016/010368, 10 pages.

AUTOMATIC CONSTRUCTION OF PERSONALIZED, PEER-DERIVED MESSAGES FOR MOBILE HEALTH APPLICATIONS

CROSS-REFERENCE TO RELATED APPLICATION(S) AND CLAIM OF PRIORITY

This application claims priority under 35 U.S.C. §119(e) to U.S. Provisional Patent Application No. 62/233,237 filed on Sep. 25, 2015 entitled AUTOMATIC CONSTRUCTION OF PERSONALIZED, PEER-DERIVED MESSAGES FOR MOBILE HEALTH APPLICATIONS. The above-identified provisional patent application is hereby incorporated by reference in its entirety.

TECHNICAL FIELD

Embodiments of the present application relate generally to communications via a network and, more specifically, to a systems and methods for automatic construction of personalized, peer-driven messages for mobile health applications.

BACKGROUND

Mobile health applications running on modern smartphones enable medical providers (such as physicians and nurses) to perform important functions that aid the health of their patients, such as monitoring the patients' levels of exercise and exchanging information related to ongoing treatment. A particular application is that of prescriptive intervention, whereby an electronic message sent by (or on behalf of) the medical provider contains information that serves to motivate, inform, or warn the patient in order to improve his or her health as part of a preventive care program. Given the ubiquity and popularity of smartphones, many hospitals and clinics are already implementing such systems (e.g., sending SMS text messages on a daily basis to remind the patient, who is a user of a smartphone, to reduce smoking).

Current mobile health intervention messaging lack personalization, however, something that is desired by patients to help motivate them. Given the need to provide preventive care to hundreds or thousands of patients, it is understandable that medical providers may not have the time or other resources to create personally-written messages for each patient. As a result, it is commonly the case that messages are generic, pre-written, and derived from standard medical suggestions, such as those from the National Institute of Health. Examples of such messages include "eat fish instead of beef," "less smoking will reduce the risk of heart attack," and "walk for 30 minutes each day." Clinical trials have already found that patients desire more personalization that will help them reach their health goal, such as reducing weight or smoking less.

SUMMARY

In a first embodiment, a non-transitory computer readable medium embodying a computer program is provided. The computer program includes computer readable program code that, when executed by processing circuitry, causes the processing circuitry to obtain a set of users as a function of profile records regarding a plurality of users. The computer program includes computer readable program code that, when executed by processing circuitry, causes the processing circuitry to define a subset of the users as a peer group based on peer group formation features by applying a clustering algorithm to profile records of the set of users. The computer program includes computer readable program code that, when executed by processing circuitry, causes the processing circuitry to calculate a peer group metric value for the peer group based on behaviors of the subset of users in the peer group. The computer program includes computer readable program code that, when executed by processing circuitry, causes the processing circuitry to calculate a user metric value for a target-user included in the subset based on behavior of the target-user. The computer program includes computer readable program code that, when executed by processing circuitry, causes the processing circuitry to construct a message relating the user metric value to the peer group metric value.

In a second embodiment, an apparatus includes computer processing circuitry. The computer processing circuitry is configured to obtain a set of users as a function of profile records regarding a plurality of users. The computer processing circuitry is configured to define a subset of the users as a peer group based on peer group formation features by applying a clustering algorithm to profile records of the set of users. The computer processing circuitry is configured to calculate a peer group metric value for the peer group based on behaviors of the subset of users in the peer group. The computer processing circuitry is configured to calculate a user metric value for a target-user included in the subset based on behavior of the target-user. The computer processing circuitry is configured to construct a message relating the user metric value to the peer group metric value.

In a third embodiment, a method implemented by at least one server is provided. The method includes obtaining a set of users as a function of profile records regarding a plurality of users. The method includes defining a subset of the users as a peer group based on peer group formation features by applying a clustering algorithm to profile records of the set of users. The method includes calculating a peer group metric value for the peer group based on behaviors of the subset of users in the peer group. The method includes calculating a user metric value for a target-user included in the subset based on behavior of the target-user. The method includes constructing a message relating the patient metric value to the peer group metric value.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
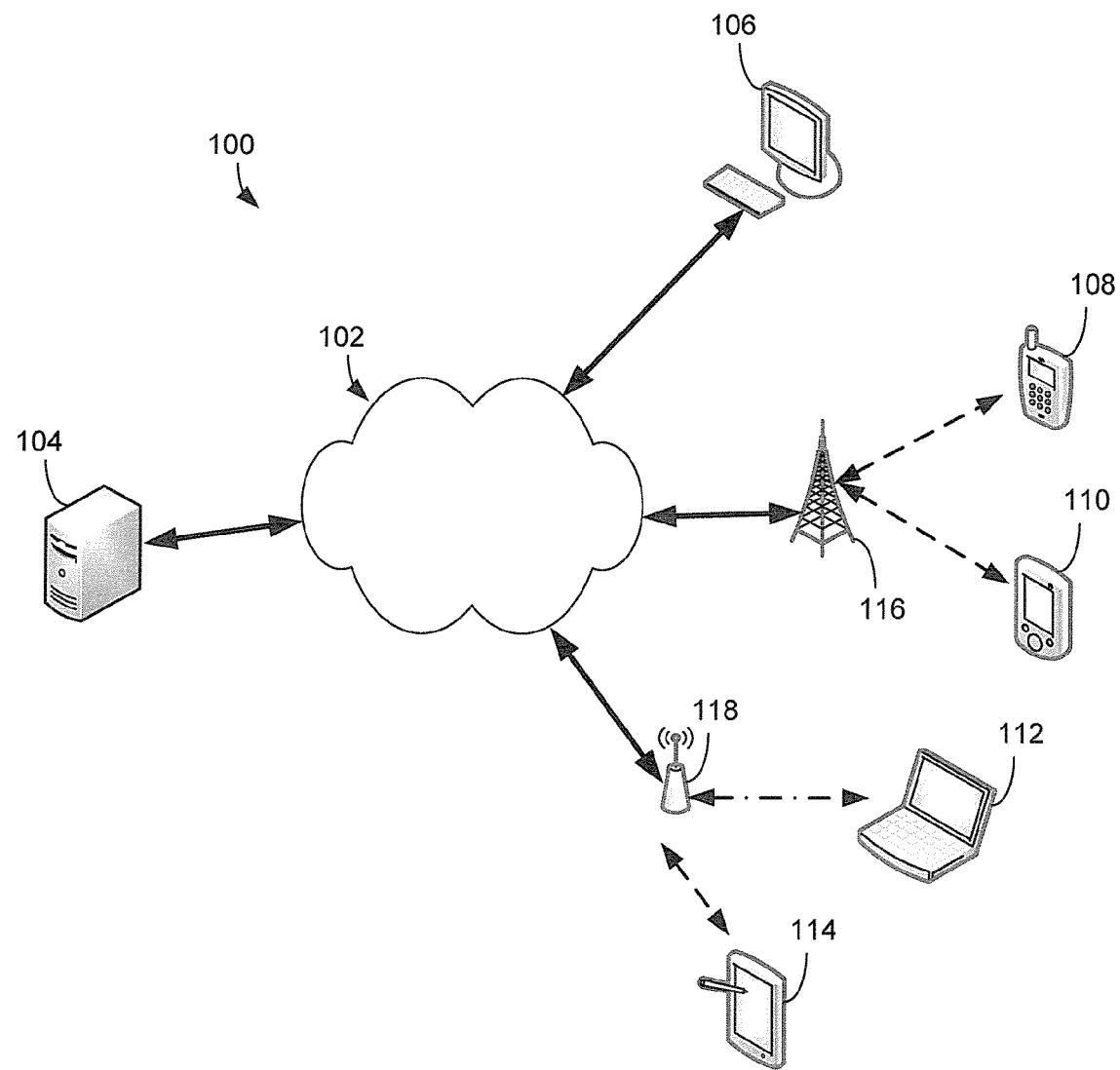
FIG. 1 illustrates an example computing system according to this disclosure.

FIGS. 1 through 8B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device or system.

As described above, patients desire more personalization that will help them reach their health goals, such as reducing weight or smoking less. This disclosure provides a solution to automatically generate tailored messages that will help motivate patients enrolled in mobile healthcare programs (also referred to as remote patient monitoring service).

Embodiments of the present disclosure provide a method and system to automatically create personalized peer-driven messages for mobile health applications. Certain embodiments apply or utilize a psychology that peer-challenge or peer-pressure is a strong motivator for people to achieve goals. Certain embodiments of the present disclosure use this psychology by constructing messages that place the user's current health achievements in the context of peers and urge the user to meet further goals. For example, a patient's current health performance or achievements can be compared and contrasted with the performance or achievements of other similarly or non-similarly situated patients or users to provide guidance messaging for use by the patient. An example of such a message is "Your peers have been averaging 15,000 walking steps each day, but you have been averaging only 9,500 steps each day. Can you catch up?"

Another example of such a message is "Your peers consume about 1900 calories on Thanksgiving. Can you watch what you eat?"

Certain embodiments of this disclosure automatically determine a user's peer group based on attributes relevant to the health goal, such as an age attribute, gender attribute, body mass index (BMI) attribute (in units of kg/m2), and disease attribute (e.g., diabetes or obesity). Examples of non-biological contextual information related to these attributes include: a user's lifestyle (e.g. sedentary or active), location, and the day, month, or season that messages are generated. Certain embodiments of this disclosure calculate a representative metric from that peer group that is relevant to the user's health. Metrics can include average step count per day, average calories consumed per day, and number of cigarettes smoked per week. Calculations can include an average or percentile descriptive statistics to represent the peer group. Certain embodiments of this disclosure generate a message that is sent to the user, or retrieved by the user, that relates the peer group's representative metric to the user's own metric. For example, the message can relate to such representative metrics as an average step count per week for the peer group. Given that the users in the peer group compete with the other users in the peer group, the desired end result is that the health of the entire peer group will increase as a whole over time.

An influential power of the messages derives from the fact that the user is compared to others in his or her peer group. Descriptive norm messages have been found to increase performance on a repeat muscular endurance take. An example of a descriptive norm message is "Your friends are exercising. So should you." By way of comparison, an example injunctive norm message is "Your friends will disapprove of you if you don't exercise enough."

FIG. 1 illustrates an example computing system 100 according to this disclosure. The embodiment of the computing system 100 shown in FIG. 1 is for illustration only. Other embodiments of the computing system 100 could be used without departing from the scope of this disclosure.

As shown in FIG. 1, the system 100 includes a network 102, which facilitates communication between various components in the system 100. For example, the network 102 may communicate Internet Protocol (IP) packets, frame relay frames, Asynchronous Transfer Mode (ATM) cells, or other information between network addresses. The network 102 may include one or more local area networks (LANs), metropolitan area networks (MANs), wide area networks (WANs), all or a portion of a global network such as the Internet, or any other communication system or systems at one or more locations.

The network 102 facilitates communications between at least one server 104 and various client devices 106-114. Each server 104 includes any suitable computing or processing device that can provide computing services for one or more client devices. Each server 104 could, for example, include one or more processing devices, one or more memories storing instructions and data, and one or more network interfaces facilitating communication over the network 102.

Each client device 106-114 represents any suitable computing or processing device that interacts with at least one server or other computing device(s) over the network 102. In this example, the client devices 106-114 include a desktop computer 106, a mobile telephone or smartphone 108, a personal digital assistant (PDA) 110, a laptop computer 112, and a tablet computer 114. However, any other or additional client devices could be used in the computing system 100.

In this example, some client devices 108-114 communicate indirectly with the network 102. For example, the client devices 108-110 communicate via one or more base stations 116, such as cellular base stations or eNodeBs. Also, the client devices 112-114 communicate via one or more wireless access points 118, such as IEEE 802.11 wireless access points. Note that these are for illustration only and that each client device could communicate directly with the network 102 or indirectly with the network 102 via any suitable intermediate device(s) or network(s).

Depending on the network type, other well-known terms may be used instead of "client device," such as "user equipment," "UE," "mobile station," "subscriber station," "remote terminal," "wireless terminal," or "user device." For the sake of convenience, the terms "user equipment" and "UE" are used in this patent document to refer to any suitable computing or processing device that interacts with at least one server or other computing device(s) over the network 102, whether the UE is a mobile device, such as a mobile telephone or smartphone, or is normally considered a stationary device, such as a desktop computer or vending machine.

As described in more detail below, the system 100 performs automatic construction of personalized, peer-derived messages for mobile health applications. For example, the desktop computer 106, such as a healthcare provider terminal, may provide screen display of a list of a plurality of patients serviced by a doctor or a healthcare provider, may receive input representing a selection of one or more of the patients to be enrolled in a mobile healthcare program. The server 104 may also receive the input representing a selection of one or more of the patients to be enrolled in a mobile healthcare program, may identify and enroll the selected patients in the mobile healthcare program, and may construct a personalized, peer-derived message to be sent to the enrolled patients. For each of multiple enrolled patients selected to receive the message, the server 104 constructs a personalized, peer-derived message relating a health-related metric value (for example, number of cigarettes smoked) of that particular patient to that of the particular patient's peer group. For example, a peer-derived message related to a smoking metric, such as a number of cigarettes smoked by a particular patient relative to a patient's peer group can be generated. An enrolled patient may use a smartphone 108 to transmit information regarding behavior, such as smoking cigarettes, of that patient through the server 104 to the desktop computer 106, thereby enabling the healthcare provider to view information regarding behavior of that patient.

Although this disclosure is described in terms of a health monitoring system that implements a mobile healthcare program, this disclosure is not limited to health industry applications. Embodiments according to this disclosure can be used for any application wherein a server 104 (i) communicates with multiple UEs through a network 102 to receive information regarding users of the multiple UEs, (ii) automatically forms a peer group based on stored profile records regarding multiple users, and (iii) constructs a message relating a peer group metric value for the peer group to a user metric value of a target-user in the peer group. For example, in an education industry, the server 104 forms a peer group of student-users facing similar learning challenges according to stored student profile records, and provides performance evaluation of a target student-user related to performance of the peer group of students using metrics such as number of science projects completed, or level participation in extracurricular activities. For example, in the research industry, the server 104 may form a peer group of engineer-users whose profile records contain information regarding expertise and skill sets in design, development, and testing. The server 104 constructs a message providing a performance comparison of a target engineer-user to the peer group regarding metrics such as deliverable completed, awards received, promotion received. As another example, in the personal finance industry, the server 104 (i) communicates with UEs of shopper-users to receive spending information stored in a shopper profile, (ii) forms a peer group of shoppers with similar spending power, and (iii) constructs messages providing shopping suggestions to send to a UE of particular shopper-user, such as a target shopper-user, based on savings of the peer group, reward programs and store promotions available to the peer group to which the particular shopper belongs.

Although FIG. 1 illustrates one example of a computing system 100, various changes may be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
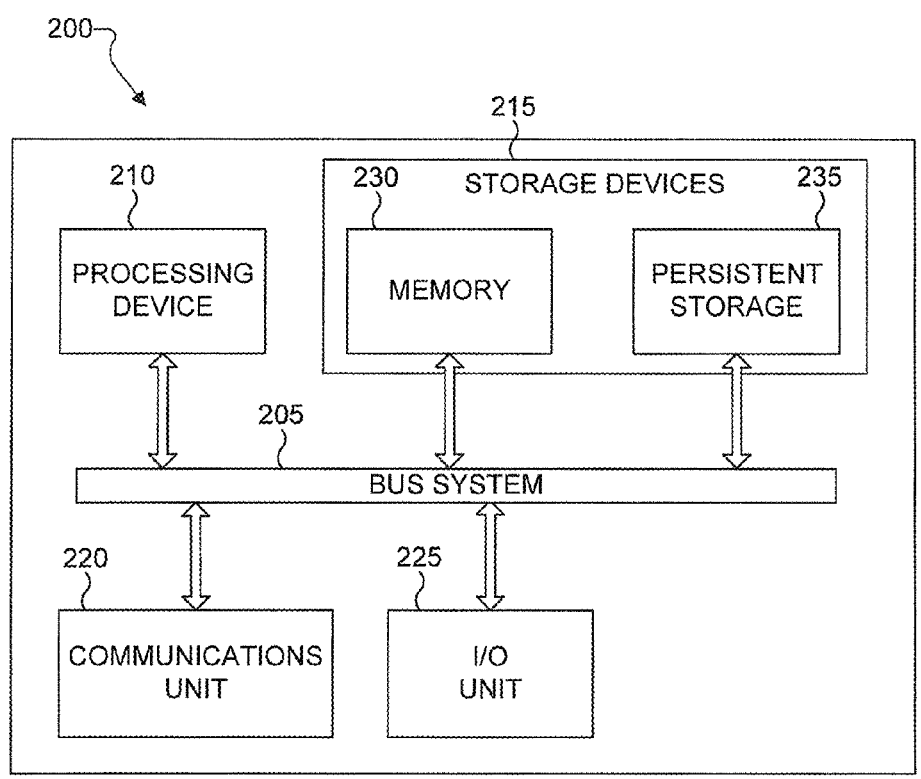
FIGS. 2 and 3 illustrate example devices in a computing system according to this disclosure.
Figure 3:
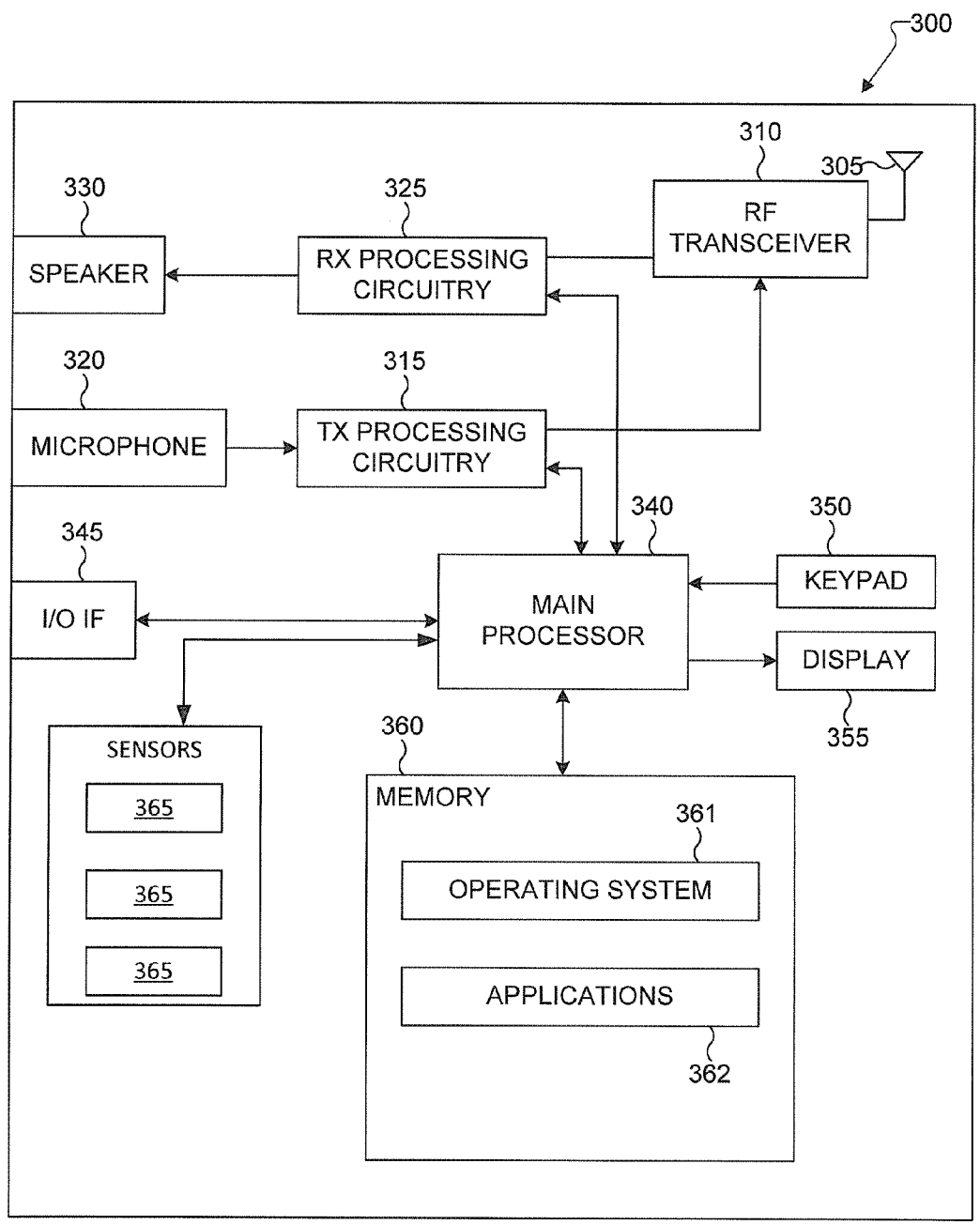

FIGS. 2 and 3 illustrate example devices in a computing system according to this disclosure. In particular, FIG. 2 illustrates an example server 200, and FIG. 3 illustrates an example UE 300. The server 200 could represent the server 104 in FIG. 1, and the UE 300 could represent one or more of the UEs 106-114 in FIG. 1.

As shown in FIG. 2, the server 200 includes a bus system 205 that supports communication between at least one processing device 210. The server 200 also includes at least one storage device 215, at least one communications unit 220, and at least one input/output (I/O) unit 225.

The processing device 210 executes instructions that can be loaded into a memory 230, such as instructions for performing automatic construction of personalized, peer-derived messages for mobile health applications. The processing device 210 may include any suitable number(s) and type(s) of processors or other devices in any suitable arrangement. Example types of processing devices 210 include microprocessors, microcontrollers, digital signal processors, field programmable gate arrays, application specific integrated circuits, and discreet circuitry.

The memory 230 and a persistent storage 235 are examples of storage devices 215, which represent any structure(s) capable of storing and facilitating retrieval of information, such as data, program code, and/or other suitable information on a temporary or permanent basis. The memory 230 can represent a random access memory or any other suitable volatile or non-volatile storage device(s). The persistent storage 235 can contain one or more components or devices supporting longer-term storage of data, such as a ready only memory, hard drive, Flash memory, or optical disc.

The communications unit 220 supports communications with other systems or devices. For example, the communications unit 220 could include a network interface card or a wireless transceiver facilitating communications over the network 102. The communications unit 220 may support communications through any suitable physical or wireless communication link(s).

The I/O unit 225 allows for input and output of data. For example, the I/O unit 225 provides a connection for user input through a keyboard, mouse, keypad, touchscreen, or other suitable input device. The I/O unit 225 can also send output to a display, printer, or other suitable output device.

Note that while FIG. 2 is described as representing the server 104 of FIG. 1, the same or similar structure could be used in one or more of the client devices 106-114. For example, a laptop or desktop computer could have the same or similar structure as that shown in FIG. 2.

As shown in FIG. 3, the UE 300 includes an antenna 305, a radio frequency (RF) transceiver 310, transmit (TX) processing circuitry 315, a microphone 320, and receive (RX) processing circuitry 325. The UE 300 also includes a speaker 330, a main processor 340, an input/output (I/O) interface (IF) 345, a keypad 350, a display 355, a memory 360, and one or more sensors 365. The memory 360 includes an operating system (OS) program 361 and one or more applications 362.

The RF transceiver 310 receives, from the antenna 305, an incoming RF signal transmitted by another component in a system. The RF transceiver 310 down-converts the incoming RF signal to generate an intermediate frequency (IF) or baseband signal. The IF or baseband signal is sent to the RX processing circuitry 325, which generates a processed baseband signal by filtering, decoding, and/or digitizing the baseband or IF signal. The RX processing circuitry 325 transmits the processed baseband signal to the speaker 330, such as for voice data, or to the main processor 340 for further processing, such as for web browsing data.

The TX processing circuitry 315 receives analog or digital voice data from the microphone 320 or other outgoing baseband data, such as web data, e-mail, or interactive video game data, from the main processor 340. The TX processing circuitry 315 encodes, multiplexes, and/or digitizes the outgoing baseband data to generate a processed baseband or IF signal. The RF transceiver 310 receives the outgoing processed baseband or IF signal from the TX processing circuitry 315 and up-converts the baseband or IF signal to an RF signal that is transmitted via the antenna 305.

The main processor 340 can include one or more processors or other processing devices and execute the OS program 361 stored in the memory 360 in order to control the overall operation of the UE 300. For example, the main processor 340 could control the reception of forward channel signals and the transmission of reverse channel signals by the RF transceiver 310, the RX processing circuitry 325, and the TX processing circuitry 315 in accordance with well-known principles. In some embodiments, the main processor 340 includes at least one microprocessor or microcontroller.

The main processor 340 is also capable of executing other processes and programs resident in the memory 360, such as operations for performing automatic construction of personalized, peer-derived messages for mobile health applications, including controlling reception of personalized, peer-derived messages from and transmission of information regarding behavior of a patient to the server 200. The main processor 340 can move data into or out of the memory 360 as required by an executing process. In some embodiments, the main processor 340 is configured to execute the applications 362 based on the OS program 361 or in response to signals received from external devices or an operator. The main processor 340 is also coupled to the I/O interface 345, which provides the UE 300 with the ability to connect to other devices such as laptop computers and handheld computers. The I/O interface 345 is the communication path between these accessories and the main controller 340.

The main processor 340 is also coupled to the keypad 350 and the display unit 355. The operator of the UE 300 can use the keypad 350 to enter data into the UE 300. The display 355 can be a liquid crystal display or other display capable of rendering text and/or at least limited graphics, such as from web sites.

The memory 360 is coupled to the main processor 340. Part of the memory 360 could include a random access memory (RAM), and another part of the memory 360 could include a Flash memory or other read-only memory (ROM).

The one or more sensors 365 are coupled to the main processor 340 and provide sensor signals and data regarding a sensed phenomena. For example, sensor 365 may include a camera, a gesture sensor, a gyroscope or gyro sensor, an air pressure sensor, a magnetic sensor or magnetometer, an acceleration sensor or accelerometer, a grip sensor, a proximity sensor, a color sensor (e.g., a Red Green Blue (RGB) sensor), a temperature/humidity sensor, an illumination sensor, etc. The sensor 365 can further include a control circuit for controlling at least one of the sensors included therein. One or more of these sensor(s) 365 may be used to determine a task being performed by a user to identify information relevant to the task being performed. As such, the UE may take the form of a wearable electronic device, such as for example, a smart watch, smart glasses, an activity tracker, or other type of wearable device.

As described in more detail below, a healthcare provider, such as a doctor who services a plurality of patients, may input selections to the first UE 300 (for example, a healthcare provider terminal), such as a selection of one or more of the patients serviced by the doctor. The first UE 300 may provide the selection of patients to the server 200. The server 200 may enroll the selected patients in a mobile healthcare program using the selection, and may construct a personalized, peer-derived message to be sent to the enrolled patients. For each of multiple enrolled patients selected to receive the message, the server 200 constructs a personalized, peer-derived message relating a health-related metric value (for example, average number of steps per day) of that particular patient to that of the particular patient's peer group. An enrolled patient uses a second UE 300 to transmit information regarding behavior, such as walking, of that patient through the server 200 to the first UE 300 of the healthcare provider, thereby enabling the healthcare provider to view information regarding behavior of that patient.

Although FIGS. 2 and 3 illustrate examples of devices in a computing system, various changes may be made to FIGS. 2 and 3. For example, various components in FIGS. 2 and 3 could be combined, further subdivided, or omitted and additional components could be added according to particular needs. As a particular example, the main processor 340 could be divided into multiple processors, such as one or more central processing units (CPUs) and one or more graphics processing units (GPUs). Also, while FIG. 3 illustrates the UE 300 configured as a mobile telephone or smartphone, UEs could be configured to operate as other types of mobile or stationary devices. In addition, as with computing and communication networks, UEs and servers can come in a wide variety of configurations, and FIGS. 2 and 3 do not limit this disclosure to any particular UE or server.

Figure 4:
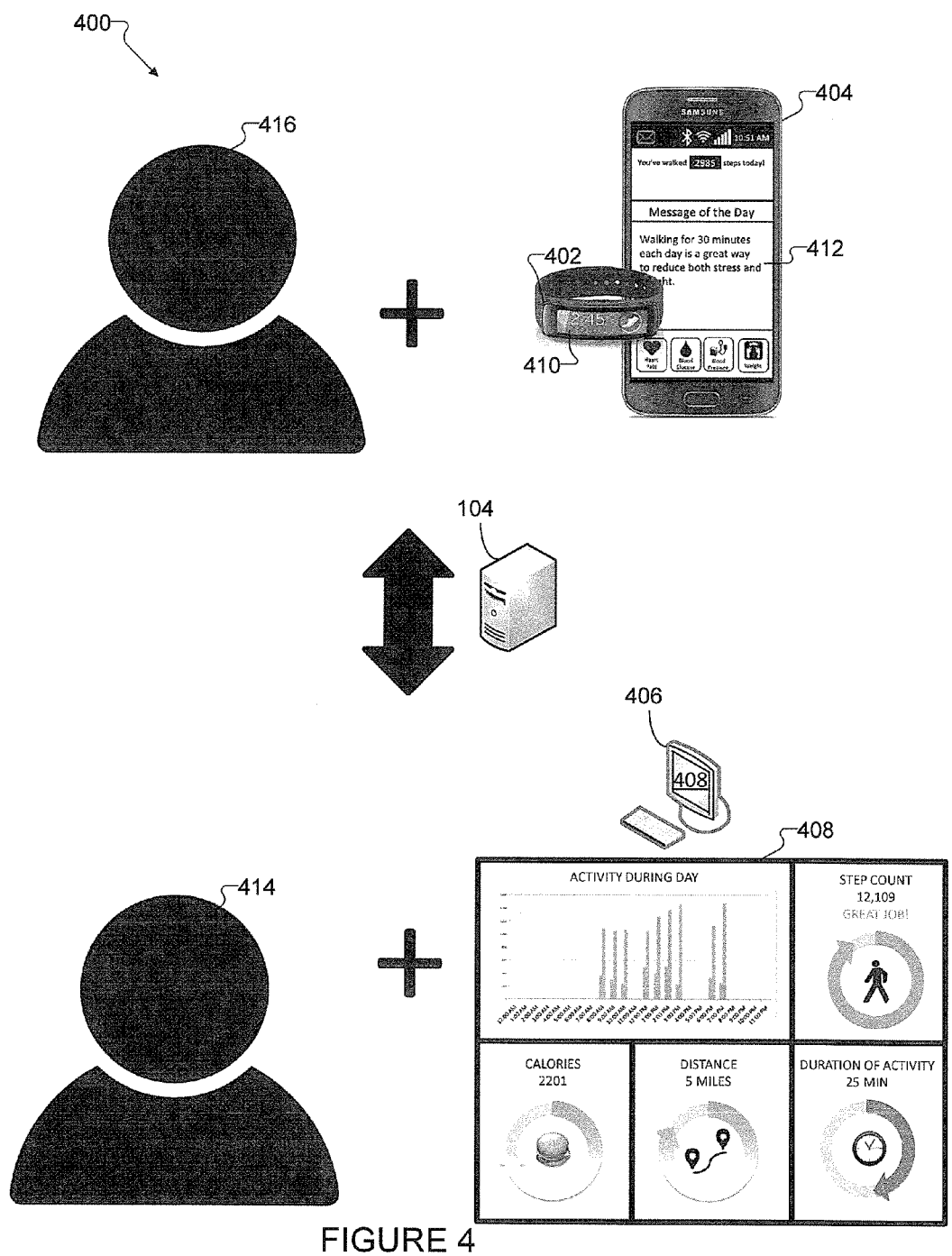
FIG. 4 illustrates communications in a health monitoring system according to this disclosure.

FIG. 4 illustrates communications in a health monitoring system 400 according to this disclosure. The embodiment of the health monitoring system 400 shown in FIG. 4 is for illustration only. Other embodiments could be used without departing from the scope of the present disclosure. The health monitoring system 400 includes user equipment of a patient, namely, a wearable device 402 and smartphone 404, one or more servers 104, and user equipment of a healthcare provider, herein referred to as a healthcare provider terminal 406. The wearable device 402, smartphone 404, and healthcare provider terminal 406 could be used with the system 100 of FIG. 1, and could be represented by the UE 300 of FIG. 3. For example, the display 355 of FIG. 3 can represent the display 408 of the healthcare provider terminal 406, the display 410 of the wearable device 402, and the display 412 of the smartphone 404. Note that the smartphone 404 in FIG. 4 could be the same as or similar to the smartphone 108 in FIG. 1; and the healthcare provider terminal 406 could be the same as or similar to the desktop computer 106 or laptop computer 112 in FIG. 1. These components 404 and 406 in FIG. 4 can operate in the same or similar manner as the corresponding components in FIG. 1.

A healthcare provider-user 414 services multiple patients, such as hundreds to thousands of patients. For example, one doctor can manage 1000-2000 patients, such that even if the doctor hires a care manager to manually type a personalized message to each of these patients, the volume of patients makes this task too great. As a solution, the healthcare provider-user 414 uses a healthcare provider terminal 406 configured to perform operations for automatic construction of personalized, peer-driven messages for mobile health applications as describe more particularly with reference to FIG. 6. For example, for a particular enrolled patient-user 416, the healthcare provider terminal 406 enables the healthcare provider-user 414 to review the behavior of the patient-user 416 on the display 408. The particular enrolled patient 416 can represent any of the multiple patients serviced by the healthcare provider-user 414.

The display 408 shows an example of physical behavior of the patient-user 416 including but not limited to: (i) a physical activity graph of number of steps taken, such as by walking, running, or climbing versus time of day or number of calories consumed versus time of day; (ii) a graphic or text indicator showing that the patient-user 416 met or exceeded a goal regarding number of steps per day; (iii) graphics showing that the patient-user 416 is close to meeting a goal regarding distance stepped in a day or regarding a number of calories consumed in a day; and (iv) a graphic showing that the patient-user 416 is not close to meeting a goal regarding a number of minutes of intense exercise in a day. In the example, shown in FIG. 4, the display 408 shows physical behavior of the patient-user 416 including: (i) a physical activity graph of number of steps taken by walking, running, or climbing versus time of day or number of calories consumed versus time of day; (ii) a graphic in the form of a full length bar in a first color, which is green, showing that the patient 416 met or exceeded the goal regarding number of steps per day by walking, running or climbing 12109 steps. The display 408 also can include a text indicator such as a "Great Job!" in the first color. The display 408 also shows additional physical behavior of the patient-user 416 including: (iii) graphics in the form of a partial-medium length bar in a second color, which is yellow, showing that the patient-user 416 approaching a 5.00 mile goal regarding distance stepped in a day or regarding a number of calories consumed or burned in a day, such as consuming or burning 2201 calories; and (iv) a graphic in the form of a partial-short length bar in a third color, which is red, showing that the patient-user 416 has performed 25 minutes of intense exercise, which is not close to meeting a goal regarding a number of minutes of intense exercise in a day.

The patient-user 416 can wear the wearable device 410 to enable the wearable device 410 to sense the physical activity of the behavior of the patient. For example, when worn by the patient-user 416, the wearable device 402 detects each step taken by the patient-user 416 and the time of day, the heart rate of the patient-user 416, and distance stepped by the patient. The wearable device 402 transmits the information regarding the behavior of the patient-user 416 to the smartphone 404 utilizing a near field communication (NFC), wireless fidelity (Wi-Fi) such as a IEEE 802.11 communication, BLUETOOTH low energy (BLE) communication, or any other suitable wireless communications protocol. The smartphone 404 transmits the information regarding the behavior of the patient-user 416 to the server 104, which allows the healthcare provider terminal 406 to access the information for display. Similarly, the displays 410, 412 of the UE 300 of the patient-user 416 can show graphics and text indicators regarding physical activity of the patient wearing the wearable device 402, such as a number of steps taken and a status bar representing how close the patient is to meeting a goal number of steps.

Although FIG. 4 illustrates one example of a health monitoring system 400, various changes may be made to FIG. 4. For example, the relative sizes, shapes, and dimensions of the various components shown in FIG. 4 are for illustration only. Each component in FIG. 4 could have any other size, shape, and dimensions. In certain embodiments, the smartphone 404 can sense the physical activity of the patient-user 416 without input from the wearable device 402. In certain embodiments, the wearable device 402 can transmit information regarding the behavior of the patient-user 416 to the server 104 without transmitting the information through the smartphone 404.

Figure 5A:
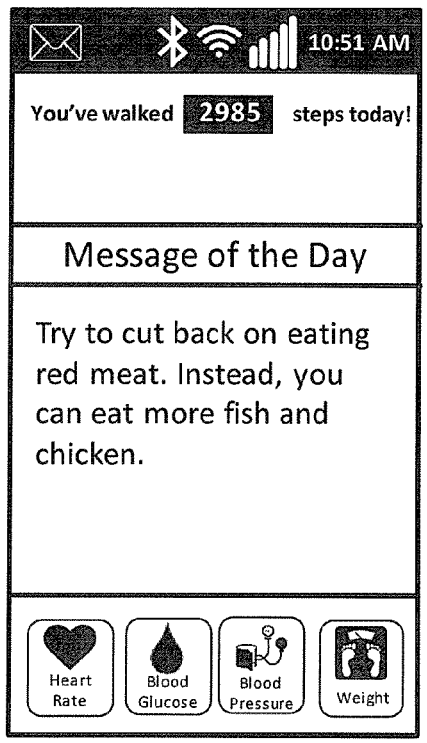
FIGS. 5A and 5B illustrate examples of a generic message of a user interface screen of a user equipment (UE) of a patient according to this disclosure.
Figure 5B:
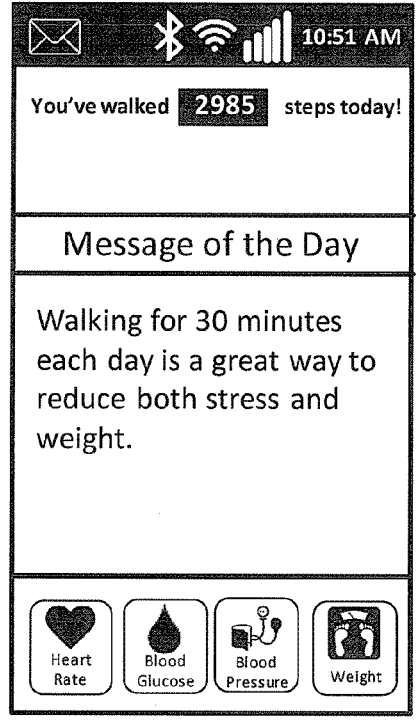

FIGS. 5A and 5B illustrate examples of a generic message of a user interface screen of a UE of a patient according to this disclosure. FIG. 5A illustrates a generic health message of a user interface screen of a UE of a patient. FIG. 5B illustrates a generic activity message of a user interface screen of a UE of a patient. The embodiments of the generic messages shown in FIGS. 5A and 5B are for illustration only. Other embodiments could be used without departing from the scope of the present disclosure.

Generic messages, including generic health messages or generic activity messages, are pre-written, generic, and derived from standard medical guidelines, such as National Institutes of Health (NIH) guidelines. Generic messages are not personalized to the particular patient-user 416, and do not relate the health-related metric of the particular patient-user 416 to a group of peers selected to be similar to the particular patient 416 based on physiological attributes or non-physiological attributes. Examples of generic messages are provided below:

Eat more fish and chicken instead of red meat.

A great way to reduce weight and your stress is to walk for 30 minutes every day.

Your diabetes needs your attention! Do your best before meals to keep your blood glucose level to be between 70 and 130.

Watch what you eat! Keep your diet focused on vegetables, whole grains, fruit, and lean white meat.

It's easy to reach 150 minutes of activity per week! That's only 30 minutes of walking for 5 days a week!

Although FIGS. 5A and 5B illustrate examples of a generic message of a user interface screen of a UE of a patient, various changes may be made to FIGS. 5A and 5B. For example, the relative sizes, shapes, and dimensions of the various components shown in FIGS. 5A and 5B are for illustration only. Each component in FIGS. 5A and 5B could have any other size, shape, and dimensions. As another example, other generic messages can be displayed.

Figure 6:
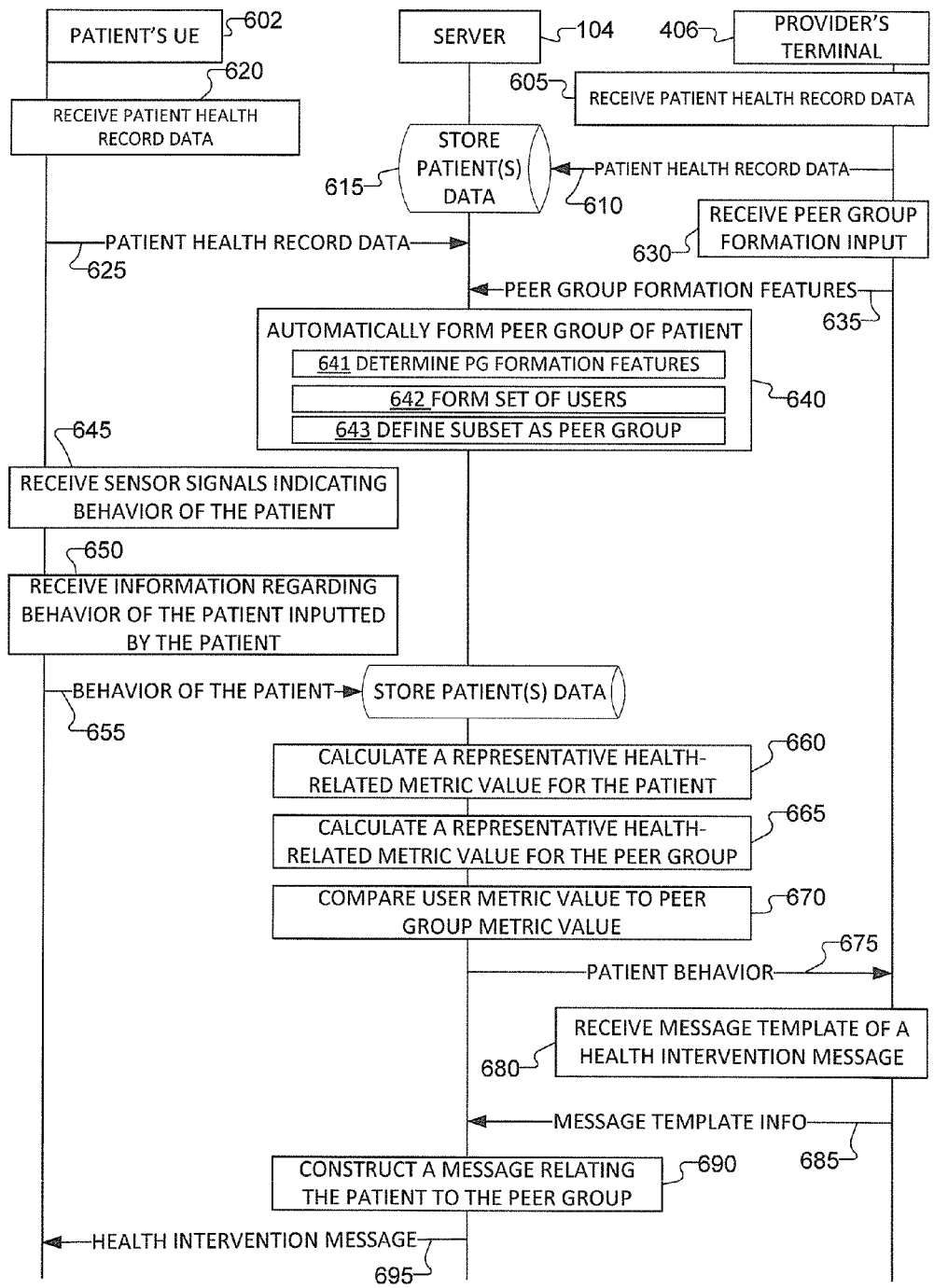
FIG. 6 illustrates a process for automatic construction of personalized, peer-derived messages for mobile health applications according to this disclosure.

FIG. 6 illustrates a process 600 for automatic construction of personalized, peer-derived messages for mobile health applications according to this disclosure. While the flow chart depicts a series of sequential steps, unless explicitly stated, no inference should be drawn from that sequence regarding specific order of performance, performance of steps or portions thereof serially rather than concurrently or in an overlapping manner, or performance of the steps depicted exclusively without the occurrence of intervening or intermediate steps. The process 600 can be implemented by the health monitoring system 400. For ease of explanation, reference number 602 will be used to refer to the UE of the patient-user, which can include the wearable device 402, the smartphone 404, or both UEs 402 and 404.

In operation 605, the healthcare provider terminal 406 receives patient health record data. For example, the healthcare provider-user 414 can input the patient health record data into the healthcare provider terminal 406 in order to enroll the patient-user 416 into the mobile healthcare program. Examples of patient health record data include identification information, physiological attributes, certain non-physiological attributes, and clinic identification information. The identification information can include first name, last name, and birth date. The physiological attributes can include age, gender, height, weight, and body mass index. Examples of non-physiological attributes include: day of the week that behavior data is generated, season or time of year that behavior data is generated, geolocation of the patient, patient lifestyle such as sedentary or active, patient disease condition such as obesity, hypertension, diabetes, and whether the patient smoked cigarettes as a teenager. The healthcare provider-user 414 inputs authentication information, such as username and personal identification number (PIN) code, for logging in to enable the healthcare provider terminal 406 to transmit data, such as the patient health record data, to the server 104.

In operation 610, the healthcare provider terminal 406 transmits the patient health record data to the server 104. The healthcare provider terminal 406 is not limited to sending one patient health record data for one patient at a time, but instead can transmit patient health record data for multiple patients.

In operation 615, in response to receiving the patient health record data, the server 104 stores the patient health record data, such as in a database. That is, for each patient-user of the multiple patients serviced by the healthcare provider-user 414, the server 104 stores the identification information of that patient in correspondence with the physiological attributes of the patient, non-physiological attributes of the patient-user, and clinic identification information.

In operation 620, the UE 602 receives patient health record data. For example, to update the values stored in the patient health records corresponding to the patient-user 416, the patient-user 416 inputs values as the patient health record data into the UE 602 using a user interface. The patient-user 416 inputs authentication information for logging in to enable the UE 602 to transmit data to the server 104.

In operation 625, the UE 602 transmits the patient health record data to the server 104. After operation 625, the server 104 repeats operation 615. In response to receiving the patient health record data from the UE 602, the server 104 stores the currently received patient health record data, thereby updating previously stored values with currently received values.

In operation 630, the healthcare provider terminal 406 receives peer group formation input specifying which peer group formation features to use to form a peer group for a patient. For example, the peer group formation input includes a selection of one or more peer group formation features (selected from a list of peer group formation features) that the server 104 will use to form a peer group for a patient. The list of peer group formation features includes various physiological attributes and various non-physiological attributes. The healthcare provider-user 414 can input an indication of whether the selection peer group formation features applies to a particular patient-user 416 or applies to multiple patients whose patient health records have a similar characteristic specified by the indication. In certain embodiments, in a similar manner, the UE 620 receives peer group formation input specifying which peer group formation features to use to form a peer group for a patient, as inputted by the patient. For example, the selection of one or more peer group formation features may specify a prioritization of or a preferred criteria for the peer group formation features.

In operation 635, the healthcare provider terminal 406 transmits the selection of peer group formation features to the server 104. The healthcare provider terminal 406 also transmits the indication of whether the selection peer group formation features applies to a particular patient-user 416 or multiple patients whose patient health records have a similar characteristic. Also in operation 635, the server 104 receives the selection of peer group formation features and the indication from the healthcare provider terminal 406. The server 104 is not limited to receiving the selection of peer group formation features from the healthcare provider terminal 406. In certain embodiments, the server 104 receives a selection of peer group formation features from another server, such as another server connected to the network 102 of FIG. 1. That is, the system 100, 400 can include a server configured to select peer group formation features from a list of peer group formation features, and transmit the selection to the server 104.

In operation 640, the server 104 automatically forms a peer group for a patient using any suitable method. The term "automatically" means without human intervention. As an example, automatically forming a peer group can mean (i) forming the peer group without using peer group formation features received from user equipment; (ii) forming the peer group without using user-inputted or without user-selected peer group formation features; or (iii) forming the peer group without using a user selection to form a peer group. Peer groups can be formed through multiple methods. The methods described in this application depend on the measurement of various attributes of both the target-user, namely, the patient for whom the messages are to be sent, and the other users who are candidates for being a part of the target-user's peer group. These attributes serve as a description for the users and are used as a basis for determining membership in a group. These attributes can be numeric or categorical, that is, non-numeric. Numeric attributes are typically measurable, such as a user's body weight, blood glucose level, or age. Categorical attributes are usually descriptive with no numeric value, such as a person having a particular set of diseases, such as hypertension and obesity. For example, based on the indication received in operation 635, the server 104 forms a peer group for the particular patient-user 416 or forms one or more peer groups for the particular patient-user 416 along with other patients having a recorded characteristic similar to the particular patient-user 416.

In certain embodiments, operation 640 includes assigning the patient-user 416 and its associated patient health record to a bucket that combines multiple discretized attributes. Attribute discretization can be implemented as value ranges, such as ranges for age, for example, 18-29, 30-39, 40-49, etc., and ranges for body mass index, such as underweight being <18.5 kg/m2, normal being 18.5-24.9, overweight being 25.0-29.9, obese being 30.0-34.9, severely obese being 35.0 or greater, etc. A particular bucket is a logical combination of individual value ranges for different attributes. Table 1 below provides an example of forming a peer group based on two peer group formation features, namely, two attributes. Each column represents age buckets, while each row represents BMI buckets. Each value in the body of Table 1 represents an example quantity of users that have a certain combination of age range and BMI range. For example, if a user is 34 years old and has a BMI of 26.1, then the user is assigned to the bucket of users having an age range of 30-39 and BMI range of 25.0-29.9. A peer group can thus be formed of the other users sharing the same attributes, namely assigned to the same bucket. As shown in Table 1, there are seventeen users in the 40-49 age group 18.5-24.9 BMI group. These seventeen users can thus be considered peers. That is, each value in the body of Table 1 represents a peer group that contains that quantity of users. When the server 104 uses more peer group formation features, the table would contain higher dimensionality, and the bucketing process applies in the same manner.

TABLE 1

Peer Groups based on two Attributes

|  |  | Age Group | | | | |
| --- | --- | --- | --- | --- | --- | --- |
|  |  | 18-29 | 30-39 | 40-49 | 50-59 | 60+ |
| Body | <18.5 | 9 | — | — | — | — |
| Mass | 18.5-24.9 | — | 14 | 17 | — | — |
| Index | 25.0-29.9 | — | 22 | 13 | 8 | — |
|  | 30.0-34.9 | — | 5 | 9 | 11 | — |
|  | 35.0+ | — | — | — | 9 | — |

In certain embodiments, operation 640 includes operations 641, 642, and 643, as such, the server 104 is configured to apply a clustering algorithm to form one or more peer groups. In operation 641, the server 104 determines which peer group formation features to use to as a basis for forming a peer group. In certain embodiments, the server 104 can determine to use the peer group formation features selected by computer processing circuitry within the server 104 itself. In certain embodiments, the server 104 can determine to use the peer group formation features selected by another server. In certain embodiments, the server 104 can determine to use the peer group formation features received from a healthcare provider terminal 406. In certain embodiments, server 104 can determine to use a combination of (i) the selection peer group formation features received from a healthcare provider terminal 406 and (ii) the peer group formation features selected by a server.

In operation 642, the server 104 forms a set of users. For example, the server 104 forms the set of users as a function of patient health records regarding a plurality of patients. For example, the set of users can include as few as zero or as many as the number of patients whose patient health records are stored in the health monitoring system 400. In certain embodiments, for each of the determined peer group formation features, the server 104 can use the function to select patient health records that include attributes similar to the particular patient's patient health record for inclusion in the set of users. As a particular example, (i) the determined peer group formation features includes age, gender, and current month, (ii) the function includes same age, same gender, and same month, the patient-user 416 is a 55 year old male currently enrolled in the mobile healthcare program in May 2015, then the server 104 forms a set of users that includes all patients whose patient health records indicate age 55, male gender, and active enrollment in May 2015.

This disclosure is not limited to forming a peer group having similar characteristics to the patient-user 416. In certain embodiments, for each of the determined peer group formation features, the server 104 can use the function to select for the set of users to include patient health records that correspond to a goal of the patient, which may be records containing attributes dissimilar from the particular patient-user's 416 patient health record. For example, the patient-user 416 may be 10 pounds overweight and have a routine of consuming an excess of 700 calories per day, and may have an intermediate goal of obtaining a normal weight. In this case, the server 104 may use the function to select patient health records that include a normal weight or a weight that is approximately 10 pounds less than the patient-user's 416 initial weight, as opposed to a similarly over-weight record. Accordingly, any subset of the set of users would include peers that are more active, to encourage the patient-user 416 to change behaviors or to change lifestyle.

In operation 643, the server 104 defines a subset of the set of users as a peer group. The definition of the subset is based on the determined peer group formation features, and the subset can be defined by applying a clustering algorithm to patient health records of the set of users. In certain embodiments of this disclosure, the subset is defined such that the peer group includes less than the whole set of users. In other embodiments of this disclosure, the subset is defined such that the peer group includes the whole set of users. The output of the clustering algorithm identifies one or more subsets of patients whose patent health records are clustered near each other in a multi-dimensional clustering in metric space 700, as described below in FIG. 7. Examples of clustering algorithms include k-Means, k-Medoids, and Agglomerative Clustering. In these clustering algorithms the selection of users belonging to the same cluster is based on the "closeness" of the plotted patient health records 725a-725e and 730a-730d, using a metric-space distance. Such algorithms are effective in creating clusters, which herein defines a subset of records as a peer group.

In certain embodiments, the definition of the subset is based on a set of group formation parameters, such as a constraint, i.e., maximum or minimum, on the density of members per peer group, a limit on the total number of peer groups to be formed, or a setting on the variance between a peer group centroid value and a corresponding value in a patient health record. As a continuation of the particular example described above in reference to operation 642, the example set of group formation parameters includes a maximum of two peer groups, in which case, the server 2104 applies a clustering algorithm to the patient health records that indicate age 55, male gender, and active enrollment in May 2015. As a result, a first peer group 705 includes a first subset of patients whose patient health records are clustered about a first centroid 710, and a second peer group 715 includes a second subset of patients whose patient health records are clustered about a second centroid 720.

In operation 645, the UE 602 receives a sensor signals indicating behavior of the patient-user 416. For example, the UE 602 worn by the patient-user 416 senses the body temperature, number of steps taken, or heart rate by receiving sensor signal generated in response to behavior of the patient. The method 600 can proceed to operation 655, wherein the UE 602 transmits information regarding behavior of the patient to the server 104, which in response to receipt, stores the received information in the patient health record of the patient-user 416.

In operation 650, the UE 602 receives information regarding behavior of the patient inputted by a user, such as the patient-user 416. For example, the patient-user 416 can use a user interface screen of the UE 620 to input information regarding consumption of a small Granny Smith apple that contains eighty-eight calories at 10:30 p.m., or to input information regarding number of cigarettes smoked. The method 600 can proceed to operation 655, as described above.

In operation 660, the server 104 calculates a representative health-related metric value for the patient 416, namely, a patient metric value that is relevant to the patient's health. The server 104 uses the information regarding the behavior of the patient to perform this calculation. Examples of a representative health-related metric value include a statistical value, e.g., average, median, maximum, regarding number of steps taken per day, number of calories consumed within a time period, a number of cigarettes smoked, a 10th, 50th, or 90th percentile ranking among peers in the patient-user's 416 peer group for a particular behavior for which a metric is measured. The patient metric value can be selected by the healthcare provider-user 414 as the standard or benchmark by which success is measured. For example, the number of steps taken per day, as measured by an accelerometer in the UE 620, can be used to measure an amount of exercise performed by the patient-user 416. As another example, the amount of calories consumed, as measured by matching the food in a patient's journal to an item in a list of known food, such as a McDonald's® Big Mac® hamburger, can be used to measure the amount of food eaten or number of calories consumed.

In certain embodiments, the server 104 can filter the data or values within patient health records to match additional context. For example, if a message is to be sent during the Christmas holiday, the peer data, i.e., data or values within patient health records of a peer group may be filtered to include only data from previous Christmas holiday seasons based on the reasoning that the behavior of users may be different during this relaxed season than during a more active summer season or during a non-holiday season. That is, calculations of metric values can be based on a filtered data set.

In operation 665, the server 104 calculates representative health-related metric value for the peer group of the patient-user 416. That is, the server 104 calculates the same representative health-related metric for the peer group of the patient-user 416 to determine a peer group metric value. The server 104 is not limited to calculating the same representative health-related metric for the patient and the peer group, and can also calculate different representative health-related metrics. As an example, the server 104 can calculate the total weight-loss or rate of weight-loss for each patient health record in the peer group, identify the top 10% of patients that have lost the most pounds or lost pounds the fastest, calculate one or more behaviors commonly performed by the identified top 10%, and assigned at least one of the behaviors as the peer group metric value. The peer group metric value can be computed through descriptive statistics. For example, the average value or mean value can be computed, for example, the average number of steps per day across all members of the peer group, as measured over the trailing 30-day period. The mean value can be skewed due to outliers in the data set. As another example, the 50th percentile value or median value can instead be found, thereby representing the value for which half the other data points is higher than the median and the other half is lower. In another example, a distribution of values can be computed in order to provide a better understanding of the other users in the peer group. Such a distribution can be in the form of values at multiple percentiles, e.g., at the 10th, 25th, 50th, 75th, and 90th percentiles, or in the form of a histogram of values.

In operation 670, the server 104 compares the patient metric value to the peer group metric value. For example, server 104 takes the patient metric value of the average number of steps per day in comparison to the average number of steps per day for the members of the peer group of the patient-user 416 in order to calculate the percentile rank of the patient-user 416.

In operation 675, the server 104 transmits information regarding behavior of the patient-user 416 to the healthcare provider terminal 406. The patient behavior information transmitted to the healthcare provider terminal 406 can include information that the server 104 received in operation 655. Additionally, the patient behavior information transmitted to the healthcare provider terminal 406 can include one or more representative health-related metric values of the patient alone or in relation to the peer group. For example, the server 104 can transmit information regarding behavior of the patient-user 416 including the graphic 810 of patient steps and peer group steps versus time, which is described more particularly below with reference to FIG. 8B. As described above, the display 408 can show information regarding the behavior of the patient-user 416, enabling the healthcare provider-user 414 to review and monitor the patient's health.

In operation 680, the healthcare provider terminal 406 receives message template information specifying content of a heath intervention message, which can be inputted to the healthcare provider terminal 406 by the healthcare provider-user 414. The message template information is configured to be used by the server 104 to construct a text message relating the patient-user 416 to the peer group of the patient. The message template information can include text for a text message, fields to be populated according to values stored in the patient health record, or a graphic, such as the graphic 810 in FIG. 8B. The message template information specifies at least one health-related metric of the patient-user 416 and at least one health-related metric of the patient-user's 416 peer group. Below are examples of message template information configured to construct a text message relating the patient-user 416 to the peer group of the patient:

You are averaging [FIELD1 of average steps per day of patient] steps per day, which is below the average of [FIELD2 of average steps per day of peer group] steps per day among your peers. Can you catch up?

Your peers consume [FIELD3 of average calories consumed by peer group on the fourth Thursday of November] calories on Thanksgiving. Can you keep below that? You consume [FIELD4 average calories consumed per day by patient] calories on an average day.

A message template allows metric values to be filled in using computed data. For example, to form the first message, a template can be created using the following notation, taken from the C programming language: "You are averaging % d steps per day, which is well below the average of % d steps per day among your peers. Can you catch up?" Values can be placed into the message replacing the "% d" strings, where the first replaced value is the representative metric for the user, and the second replaced value is the representative metric for the peer group.

In operation 685, the healthcare provider terminal 406 transmits the message template information to the server 104, which receives the same. In operation 690, the server 104 constructs a message relating a health-related metric of the patient-user 416 to the health-related metric of the peer group of the patient-user 416. In other words, in the message, the patient-user's 416 progress is stated with respect to the peer group's representative. More particularly the server 104 constructs the message according to specifications within the received message template information. For example, the information regarding behavior of the patient-user 416 may enable the server 104 to calculate an average of 9,200 steps per day and 2,300 calories per day, while the information regarding the behavior of the patient-user's 416 peer group may enable the server 104 to calculate an average of 18,300 steps per day and 3,200 calories consumed the fourth Thursday of November. Accordingly, the server 104 constructs a text or graphic message by populating the fields of the message template information with specified calculations or values.

This disclosure is not limited to constructing messages according to specifications within the received message template information. In operation 690, the server 104 can monitor behaviors of the patient-user 416 and behaviors of the patient-user's 416 peer group to determine when a condition is met, and in response to determining that the condition is met, select a message template, from a list of one or more message templates, that corresponds to meeting the condition, and construct a message according to the selected message template. The list of message templates makes a meaningful comparison or recommendation relating a health-related metric of the patient-user 416 to the health-related metric of the peer group of the patient-user 416. Note that the text message transmitted to the UE 602 is constructed in natural language, for example "You are averaging 9,200 steps per day, which is below the average of 18,300 steps per day among your peers. Can you catch up?"

In operation 695, the server 104 conveys the constructed health intervention message to the UE 602. According to various embodiments of this disclosure, conveyance of the constructed health intervention message to the UE 602 can be in multiple manners, such as a push message, as a pull message, retrieve on demand message, or as a pre-retrieved message. That is, the server 104 can transmit the message the message to the UE 602, or the UE 602 can retrieve the message from the server 104. In certain embodiments, the personalized, peer-derived message can be sent to the patient each morning using an SMS text message or an application push notification, such as through Google Cloud Messaging. The message can also be sent at other times of the day to coincide with the patient's desired health target. For example, a personalized, peer-derived message relating the patient's average caloric intake relative to the peer group can be delivered at around meal times, such as right before lunch and dinner. These meal times can be standard or alternatively determined as a function of meal times recorded in the patient's food journal. In certain embodiments, the UE 602 pulls information from the computer server 104 at a convenient time. For example, while the patient-user 416 is preparing to go jogging, the UE 602 can query a Web server (such as the server 104) managed by the health provider-user 414, and the Web server can deliver a relevant personalized, peer-derived message relating the user's current health metric to that of the peer group. Below are examples of the constructed (i.e., personalized, peer-derived) health intervention messages:

You are averaging 9,200 steps per day, which is below the average of 18,300 steps per day among your peers. Can you catch up?

Your peers consume 3,200 calories on Thanksgiving. Can you keep below that? You consume 2,300 calories on an average day.

You are leading your peer group with 27,000 steps per day. But the second-place member's step count average has increased from 21,200 to 25,500 steps per day over the last two weeks. Can you stay ahead?

Although FIG. 6 illustrates one example of a process 600 for automatic construction of personalized, peer-derived messages for mobile health applications, various changes may be made to FIG. 6. For example, while shown as a series of steps, various steps in FIG. 6 could overlap, occur in parallel, occur in a different order, or occur any number of times. As an example, the process 600 is not limited to having one server 104, but instead, a plurality of servers (connected via the network 102) can perform various functions of the server 104. For example, a server 104 may receive patient heath record data, and other server may form a peer group, and another server may control the storage of patient data. In certain embodiments, the UE 602 of the patient (i.e., target-user) replaces and performs the operations of the healthcare provider's terminal 406. For example, the patient-user 416 uses the UE 602 to self-enroll in the mobile healthcare program, and the UE 602 receives information regarding patient behavior in operation 675.

According to various embodiments of this disclosure, a system is provided. The system includes at least one server configured to obtain a set of users as a function of profile records regarding a plurality of users. The system includes at least one server configured to define a subset as a peer group based on peer group formation features by applying a clustering algorithm to profile records of the set of users. The system includes at least one server configured to calculate a peer group metric value for the peer group based on behaviors of the subset of users in the peer group. The system includes at least one server configured to calculate a user metric value for a target-user included in the subset based on behavior of the target-user. The system includes at least one server configured to construct a message relating the user metric value to the peer group metric value. The at least one server can include a first server configured to perform at least some of the operations of the at least one server, and a second server configured to perform a remainder of the operations of the at least one server.

Figure 7:
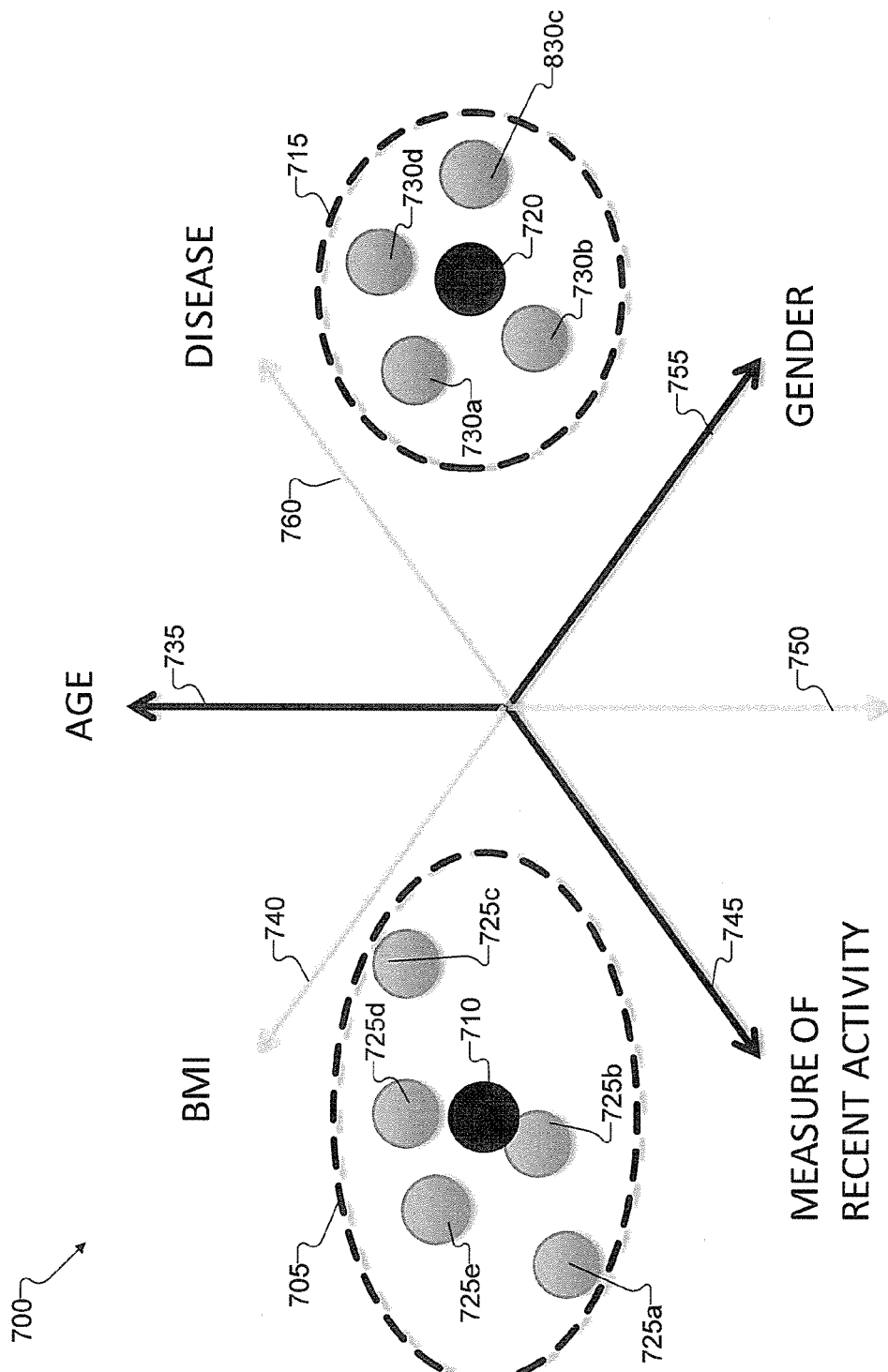
FIG. 7 illustrates a multi-dimensional clustering in metric space according to this disclosure.

FIG. 7 illustrates a multi-dimensional clustering in metric space 700 according to this disclosure. The embodiment of the metric space 700 shown in FIG. 7 is for illustration only. Other embodiments could be used without departing from the scope of the present disclosure.

To determine peer groups 705 and 715, the server 104 uses the multi-dimensional clustering in metric space 700 in which each patient health record can be plotted according to each axis. That is, each of the plotted patient health record stores a value corresponding to each axis in the multi-dimensional clustering in metric space 700. The server 104 defines a subset of patient health records that establish a peer group by applying a clustering algorithm to the plotted patient health records. In the example shown, patient health records representing patients (i.e., profile records representing users) are plotted and clustered by 6 attributes, wherein a dotted line identifies each cluster. Each cluster is also described by a centroid, which is a representative center of mass for the cluster. In the example shown, the clustering algorithm results include a subset of plotted patient health records 725a-725e clustered about the first centroid 710 and another subset of plotted patient health records 730a-730d clustered about the second centroid 720. That is, the first peer group 805 includes the subset of plotted patient health records 725a-725e regarding a corresponding subset of patients, and the second peer group includes the other subset of plotted patient health records 730a-730d regarding the other corresponding subset of patients.

Each axis represents one of the peer group formation features that the server 104 has determined to use as a basis for forming a peer group. In the example shown, a first axis 735, which is the age axis, corresponds to the peer group formation feature of age, the second axis 740, which is the BMI axis, corresponds to the peer group formation feature of body mass index, the third axis 745, which is the measure of recent activity axis, corresponds to the peer group formation feature of steps taken per day, the fourth axis 750, which is the geolocation axis, corresponds to the peer group formation feature of geolocation, the fifth axis 755, which is the gender axis, corresponds to the peer group formation feature of gender, and the sixth axis 760, which is the disease axis, corresponds to the peer group formation feature of disease.

In clustering algorithms, a distance value is computed between each pair of plotted patient health records. In one embodiment of this disclosure, a Euclidean distance value is computed according to Equations 1 and 2 (below). In Equations 1 and 2, $d(\vec{p},\vec{q})$ and $d(\vec{q},\vec{p})$ represents the distance between the attribute vectors p and q. The distance is the square root of the sum of squared differences between each attribute value.

$$d(\vec{p}, \vec{q}) = d(\vec{q}, \vec{p}) = \sqrt{(q_1 - p_1)^2 + (q_2 - p_2)^2 - \ldots + (q_n - p_n)^2} \quad (1)$$

$$d(\vec{p}, \vec{q}) = d(\vec{q}, \vec{p}) = \sqrt{\sum_{i=1}^{n} (q_i - p_i)^2} \quad (2)$$

In order to use Euclidean distance effectively for clustering, the server 104 performs some data pre-processing beforehand. Numerical data can be standardized; that is, each attribute value can be modified such that for a given attribute, the values have a mean of 0.0 and a standard deviation of 1.0. This pre-processing can be performed using Equation 3 (below).

$$\text{standardizedValue} = (\text{originalValue} - \text{mean})/\text{standardDeviation} \quad (3)$$

The effect of this pre-processing is that the value units are in standard deviations from the mean. Categorical attribute data can also be pre-processed in order for categorical values (such as having hypertension or obesity) to have a distance value. For example, each categorical attribute can be binarized into having the attribute or not. For example, the attribute of hypertension can be binarized to two values: 1 for having hypertension and 0 for not having hypertension. Such binarization can be applied to all categorical attributes, and once done, categorical and numerical attributes may be used for Euclidean distance calculations.

Although FIG. 7 illustrates one example of a multi-dimensional clustering in metric space 700, various changes may be made to FIG. 7. For example, the relative sizes, shapes, and dimensions of the various components shown in FIG. 7 are for illustration only. Each component in FIG. 7 could have any other size, shape, and dimensions. For example, more or fewer axes can be represented. As another example, the axes can correspond to different peer group formation features (physiological attributes, non-physiological attributes).

Figure 8A:
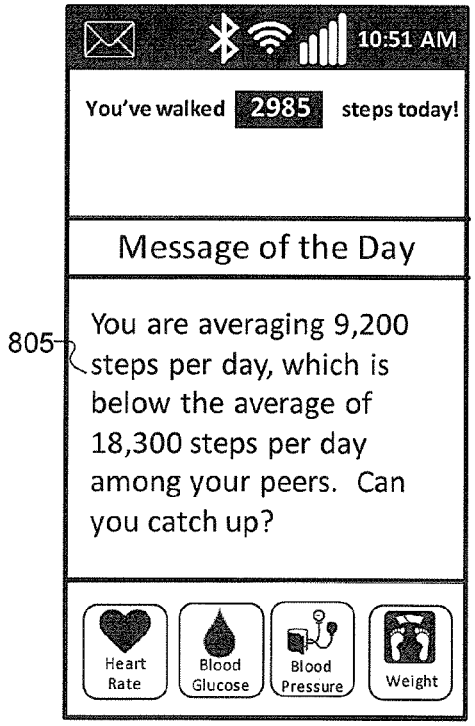
FIGS. 8A and 8B illustrate personalized, messages peer-derived messages of a user interface screen of a user equipment (UE) of a patient according to this disclosure.
Figure 8B:
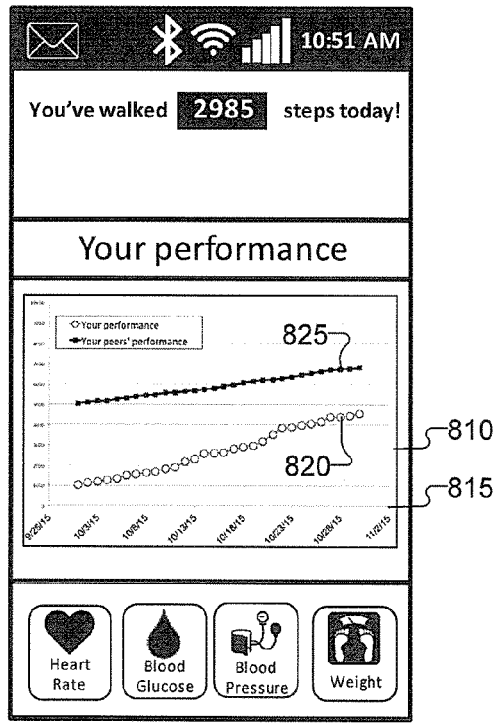

FIGS. 8A and 8B illustrate personalized, messages peer-derived messages of a user interface screen of a user equipment (UE) of a patient according to this disclosure. The embodiments of the peer-derived messages shown in FIGS. 8A and 8B are for illustration only. Other embodiments could be used without departing from the scope of the present disclosure. The FIG. 8A illustrates an example user interface screen of the UE 602 showing a text message 805 relating the patient-user 416 to the peer group of the patient. At least one server 104 of health monitoring system 400 constructs and transmits the text message 805, as described above with reference to operations 690 and 695 of FIG. 6.

FIG. 8B illustrates an example user interface screen of the UE 602 showing a graphic message 810 relating the patient-user 416 to the peer group of the patient. At least one server 104 of health monitoring system 400 constructs and transmits the graphic message 810, as described above with reference to operations 690 and 695 of FIG. 6. For example, the message template information may to be used by the server 104 to construct a graphic that includes a timeline 815, and a comparison of the patient-user's 416 representative health-related metric 820 to the peer group's representative health-related metric 825. The graphic message 810 shows the patient metric value 820 plotted over a timeline 815 of approximately January 2012 through beyond July 2013, and the peer group metric value 825 plotted over the same timeline 815.

Although FIGS. 8A and 8B illustrate one example of a text message 805 and one example of a graphic message 810, various changes may be made to FIGS. 8A and 8B. For example, the relative sizes, shapes, and dimensions of the various components shown in FIGS. 8A and 8B are for illustration only. Each component in FIGS. 8A and 8B could have any other size, shape, and dimensions. In certain embodiments, the graphic 810 can additionally or alternatively include a comparison value, such as a difference between the peer group metric value 825 and the patient metric value 820. In certain embodiments, the graphic message can include a chart (e.g., a bar chart) or a table.

Figures 9, 10:
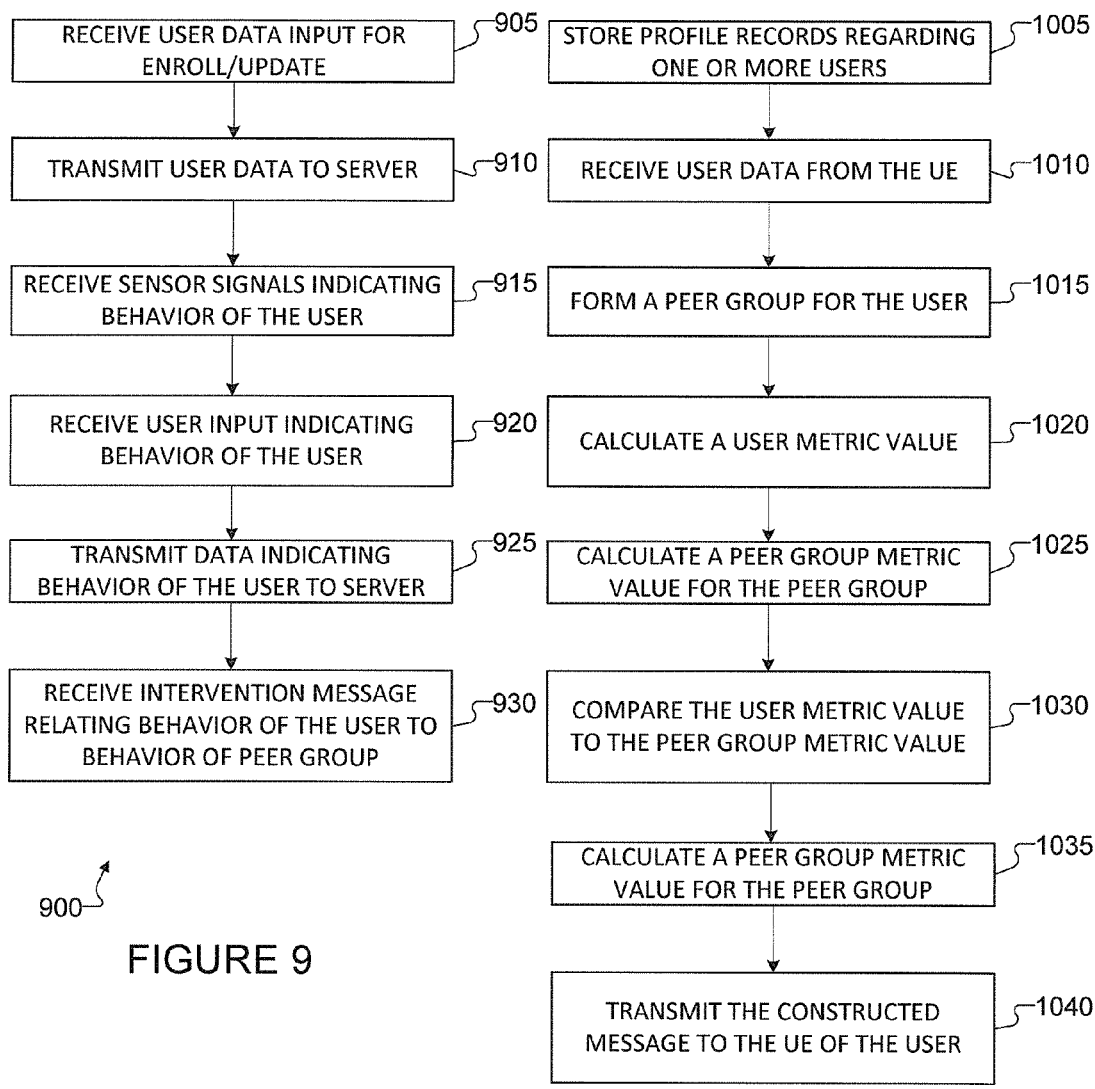
FIG. 9 illustrates a method 900 for automatic construction of personalized, peer-derived messages implemented by user equipment according to this disclosure.
FIG. 10 illustrates a method 1000 for automatic construction of personalized, peer-derived messages implemented by at least one server according to this disclosure.

FIG. 9 illustrates a method 900 for automatic construction of personalized, peer-derived messages implemented by user equipment according to this disclosure. For ease of explanation, the method 1000 will be described according to the example in which the UE 300 can communicate with the server 104 through the network 102 by implementing the method 900.

In block 905, the UE 300 receives input including user data. The user data can input through the keypad 350, or other user interface for inputting data. The user data can include information for enrollment in a program associated with automatic construction of personalized, peer-derived messages. For example, the user can use the UE 300 to self-enroll in the program that enables the UE 300 to receive an intervention message relating the user to a peer group associated with the user of the UE 300. The user data can include information stored in to a profile record regarding a user. For example, a student-user can use the UE 300 to access a user interface screen provided on the display 355 through a mobile application that enables the student-user to enroll in the program, establish a profile record, or update the profile record with the user data. Note that block 905 can include certain features described above in reference to operations 605, 620, 630.

In block 910, the UE 300 transmits the user data to the server 104. Note that block 910 can include certain features described above in reference to operations 610, 625, and 635.

In block 915, the UE 300 receives one or more sensor signals indicating behavior of the user. The sensor signals can be generated by sensors 365 within the UE 300, such as while the UE is worn by or carried by the user. The sensor signals can be received through the I/O IF 345 from a wearable device worn by the user. The sensor signals can be processed by the main processor 340 to determine a task being performed by the user/wearer. The task being performed by the user/wearer can be stored in memory 360 as behavior information. Note that block 915 can include certain features described above in reference to operation 645.

In block 920, the UE 300 receives user input indicating behavior of the user. For example, a student-user uses the keypad 350 to input information indicating a number of hours of spent participating in extracurricular activities, or number of hours spent studying. The task being performed by the user/wearer can be stored in memory 360 as behavior information. Note that block 920 can include certain features described above in reference to operation 650.

In block 925, the UE 300 transmits data indicating behavior of the user to the server 104. That is, the UE 300 transmits the behavior information to the server 104. For example, the behavior information stored in the megraphicmory 360 can be transmitted to the server 102 via the network 102. In certain embodiments, the UE 300 transmits the sensor signals to the server 104, and a signal processor within the server 104 determines the task being performed by the user/wearer. Note that block 925 can include certain features described above in reference to operation 655.

In block 930, the UE 300 receives a message relating the user metric value to the peer group metric value. The received message can be transmitted from the server 104 to the UE 300. As an example, the UE 300 can receive an intervention message relating behavior of the user to behavior of a peer group associated with the user of the UE 300. Note that block 930 can include certain features described above in reference to operation 695.

FIG. 10 illustrates a method 1000 for automatic construction of personalized, peer-derived messages implemented by at least one server according to this disclosure. For ease of explanation, the method 1000 will be described according to the example in which the server 104 can communicate with the UE 300 through the network 102 by implementing the method 1000.

In block 1005, the server 104 stores profile records regarding one or more users. For example, the profile records can be stored in a database or in a memory operably connected to the server 102. Note that block 1005 can include certain features described above in reference to operation 610 and 615.

In block 1010, the server 104 receives user data from the UE 300. For example, the server 104 can receive the user data, and the method 1000 can return to block 1005 to store it in the memory or database. The user data received is used to establish or update a profile record, which can include peer group formation features accessible to the server 104. Note that block 1010 can include certain features described above in reference to operation 610, 625, and 630.

In block 1015, the server 104 automatically forms a peer group for the user of the UE 300. That is, the server 104 obtains a set of users as a function of the profile records stored in the database; and defines a subset as a peer group based on peer group formation features. In certain embodiments, defining the subset as a peer group includes applying a clustering algorithm to profile records of the set of users. This disclosure is not limited to applying a clustering algorithm, and can define the subset as a peer group by assigning the user and/or the user's profile record to a bucket that combines multiple discretized attributes. As an example, the server can access peer group formation features within the profile record of the user of the UE 300 to determine multiple discretized attributes for forming the peer group. The profile record can include a prioritized list of peer group formation features or a list of attributes with different weights of importance to a goal of the user. Note that block 1015 can include certain features described above in reference to operation 640.

In block 1020, the server 104 calculates a user metric value for the user of the UE 300. Note that block 1020 can include certain features described above in reference to operation 660.

In block 1025, the server 104 calculates a peer group metric value for the peer group that includes the user of the UE 300. Note that block 1025 can include certain features described above in reference to operation 660.

In block 1030, the server 104 compares the user metric value to the peer group metric value. Note that block 1030 can include certain features described above in reference to operation 670.

In block 1035, the server 104 constructs a message relating the user metric value to the peer group metric value. Note that block 1035 can include certain features described above in reference to operation 690.

In block 1040, the server 104 transmits the constructed message to the UE 300.

Although FIGS. 9 and 10 illustrate example methods 900 and 1000 for automatic construction of personalized, peer-derived messages, various changes may be made to FIGS. 9 and 10. For example, while shown as a series of steps, various steps in FIGS. 9 and 10 could overlap, occur in parallel, occur in a different order, or occur any number of times. As another example, the server 104 could construct and transmit the message relating the user metric value to the peer group metric value in an audio format, and accordingly, the UE 300 could receive and playback an audio reading of the message.

Although the present disclosure has been described with embodiments, various changes and modifications may be suggested to one skilled in the art. It is intended that the present disclosure encompass such changes and modifications as fall within the scope of the appended claims.

What is claimed is:

1. A non-transitory computer readable medium embodying a computer program, the computer program comprising computer readable program code that, when executed by processing circuitry, causes the processing circuitry to:

receive a plurality of user profile records for one or more enrolled users enrolled in a mobile healthcare program;
identify a set of users from the plurality of the user profile records according to a first health related human physical attribute or a first human behavioral attribute;
create a peer group by defining a subset of the set of users according to a selected criterion and by clustering profile records of the set of users, wherein the profile records of the set of users are clustered by identifying a number of values of the selected criterion within a metric-space distance of each other and wherein the selected criterion comprises at least one of a second health related human physical attribute or a second human behavioral attribute;

calculate at least one peer group metric value for the peer group based on behaviors of the subset of users in the peer group;

calculate a user metric value for a target-user included in the subset based on a behavior of the target-user;

compare the user metric value for the target-user to the at least one peer group metric value; and construct a personalized message relating the user metric value to the peer group metric value, the personalized message configured to be transmitted wirelessly to a mobile device of the target-user and motivate the target-user to change at least one behavior.

2. The non-transitory computer readable medium of claim 1, wherein the computer program further comprises computer readable program code that, when executed by the processing circuitry, causes the processing circuitry to:
determine the selected criterion based on at least one of:
one or more features corresponding to the target-user, which are received from a user equipment, or
peer group formation features selected by the processing circuitry.

3. The non-transitory computer readable medium of claim 1, wherein the computer program further comprises computer readable program code that, when executed by the processing circuitry, causes the processing circuitry to:
adjust the clustering to form the peer group impacting a size of the peer group.

4. The non-transitory computer readable medium of claim 1, wherein the computer program further comprises computer readable program code that, when executed by the processing circuitry, causes the processing circuitry to:
transmit the personalized message to user equipment of the target-user, wherein the personalized message includes a text format or a graphic format.

5. The non-transitory computer readable medium of claim 1, wherein the computer program further comprises computer readable program code that, when executed by the processing circuitry, causes the processing circuitry to:
generate a comparison value from the comparison of the user metric value to the peer group metric value; and
wherein the personalized message includes the comparison value.

6. The non-transitory computer readable medium of claim 1, wherein the computer program further comprises computer readable program code that, when executed by the processing circuitry, causes the processing circuitry to:
receive message template information from a user equipment; and
construct the personalized message to include text specified by the message template information or a graphic specified by the message template information.

7. The non-transitory computer readable medium of claim 1, wherein the computer program further comprises computer readable program code that, when executed by the processing circuitry, causes the processing circuitry to:
transmit a plurality of instructions to a user equipment, wherein the plurality of instructions are storable in a computer readable medium, wherein the plurality of instructions are configured to cause a processor of the user equipment to:
receive user inputted data that includes at least one of:
the selected criterion or
message template information; and
transmit the user inputted data to the processing circuitry, wherein at least one server includes the processing circuitry.

8. The non-transitory computer readable medium of claim 1, wherein the computer program further comprises computer readable program code that, when executed by the processing circuitry, causes the processing circuitry to:
transmit a plurality of instructions to a user equipment of the target-user, wherein the plurality of instructions are storable in a computer readable medium, wherein the plurality of instructions are configured to cause a processor of the user equipment of the target-user to:
receive at least one of:
profile record data inputted into the user equipment of the target-user, or
the behavior of the target-user; and
transmit the inputted profile record data to the processing circuitry, wherein at least one server includes the processing circuitry.

9. The non-transitory computer readable medium of claim 1, wherein the computer program further comprises computer readable program code that, when executed by the processing circuitry, causes the processing circuitry to:
receive, from a user equipment, profile record data regarding the target-user;
store the received profile record data corresponding to the target-user in a profile record regarding the target-user in a memory; and
in response to subsequently receiving profile record data from the user equipment, update the stored profile record regarding the target-user using the subsequently received profile record data.

10. An apparatus comprising:
a transceiver configured to communicate via a wireless network; and
processing circuitry configured to:
receive a plurality of user profile records for one or more enrolled users enrolled in a mobile healthcare program;
identify a set of users from the plurality of user profile records according to a first health related human physical attribute or a first human behavioral attribute;
create a peer group by defining a subset of the set of users according to a selected criterion and by clustering profile records of the set of users, wherein the profile records of the set of users are clustered by identifying a number of values of the selected criterion within a metric-space distance of each other and wherein the selected criterion comprises at least one of a second health related human physical attribute or a second human behavioral attribute;
calculate at least one peer group metric value for the peer group based on behaviors of the subset of users in the peer group;
calculate a user metric value for a target-user included in the subset based on a behavior of the target-user;
compare the user metric value for the target-user to the at least one peer group metric value; and
construct a personalized message relating the user metric value to the peer group metric value, the personalized message configured to be transmitted wirelessly to a mobile device of the target-user and motivate the target-user to change at least one behavior.

11. The apparatus of claim 10, wherein the computer processing circuitry is further configured to determine the selected criterion based on at least one of:
one or more features corresponding to the target-user which are received from a user equipment, or
peer group formation features selected by the computer processing circuitry.

12. The apparatus of claim 10, wherein the computer processing circuitry is further configured to adjust the clustering to form the peer group impacting a size of the peer group.

13. The apparatus of claim 10, wherein the computer processing circuitry is further configured to transmit the personalized message to user equipment of the target-user, wherein the personalized message includes a text format or a graphic format.

14. The apparatus of claim 10, wherein the computer processing circuitry is further configured to:
generate a comparison value from the comparison of the user metric value to the peer group metric value; and
wherein the personalized message includes the comparison value.

15. The apparatus of claim 10, wherein the computer processing circuitry is further configured to:
receive message template information from a user equipment; and
construct the personalized message to include text specified by the message template information or a graphic specified by the message template information.

16. A method implemented by at least one server, the method comprising:
obtaining a plurality of user profile records for one or more enrolled users enrolled in a mobile healthcare program
identifying a set of users from the plurality of user profile records according to a first health related human physical attribute or a first human behavioral attribute;
creating a peer group by defining a subset of the set of users according to a selected criterion and by clustering profile records of the set of users, wherein the profile records of the set of users are clustered by identifying a number of values of the selected criterion within a metric-space distance of each other and wherein the selected criterion comprises at least one of a second health related human physical attribute or a second human behavioral attribute;
calculating at least one peer group metric value for the peer group based on behaviors of the subset of users in the peer group;
calculating a user metric value for a target-user included in the subset based on a behavior of the target-user;
compare the user metric value for the target-user to the at least one peer group metric value; and
constructing a personalized message relating the user metric value to the peer group metric value, the personalized message configured to be transmitted wirelessly to a mobile device of the target-user and motivate the target-user to change at least one behavior.

17. The method of claim 16, further comprising determining the peer group formation features based on at least one of:
one or more features corresponding to the target-user, which are received from a user equipment, or
peer group formation features selected by the processing circuitry.

18. The method of claim 16, further comprising transmitting the personalized message to user equipment of the target-user, wherein the personalized message includes a text format or a graphic format.

19. The method of claim 16, further configured to:
generate a comparison value from the comparison of the user metric value to the peer group metric value; and
wherein the personalized message includes the comparison value.

20. The method of claim 16, wherein the server is further configured to:
receive message template information from a user equipment; and
construct the personalized message to include text specified by the message template information or a graphic specified by the message template information.

21. The non-transitory computer readable medium of claim 1, wherein
an health related human physical attribute comprises one or more of: an age attribute, gender attribute, body mass index (BMI) attribute (in units of kg/m2), or a disease attribute; and
a human behavioral attribute comprises one or more of an active lifestyle, sedentary lifestyle, intermediate lifestyle, dietary habit, or geographic location.

* * * * *